(12) United States Patent
Shulock et al.

(10) Patent No.: US 11,896,476 B2
(45) Date of Patent: Feb. 13, 2024

(54) PATELLA TENDON REALIGNMENT IMPLANT WITH CHANGEABLE SHAPE

(71) Applicant: ZKR ORTHOPEDICS, INC., San Francisco, CA (US)

(72) Inventors: Damien Shulock, San Francisco, CA (US); Jeffrey Halbrecht, San Francisco, CA (US); John Barrett, San Francisco, CA (US); Katherine J. Stephenson, Belmont, CA (US)

(73) Assignee: ZKR Orthopedics, Inc., San Francisco, CA (US)

( * ) Notice: Subject to any disclaimer, the term of this patent is extended or adjusted under 35 U.S.C. 154(b) by 236 days.

(21) Appl. No.: 17/127,634

(22) Filed: Dec. 18, 2020

(65) Prior Publication Data

US 2021/0205068 A1    Jul. 8, 2021

Related U.S. Application Data

(60) Provisional application No. 62/956,562, filed on Jan. 2, 2020.

(51) Int. Cl.
*A61F 2/08* (2006.01)

(52) U.S. Cl.
CPC ..... *A61F 2/0811* (2013.01); *A61F 2002/0835* (2013.01); *A61F 2002/0858* (2013.01); *A61F 2210/0014* (2013.01); *A61F 2220/0091* (2013.01); *A61F 2250/0003* (2013.01)

(58) Field of Classification Search
CPC ............ A61F 2002/4205; A61F 2/3877; A61F 2/3868
See application file for complete search history.

(56) References Cited

U.S. PATENT DOCUMENTS

| 3,872,519 A | 3/1975 | Giannestras et al. |
| 3,879,767 A | 4/1975 | Stubstad |
| 3,886,599 A | 6/1975 | Schlein |
| 3,889,300 A | 6/1975 | Smith |
| 3,964,106 A | 6/1976 | Hutter et al. |

(Continued)

FOREIGN PATENT DOCUMENTS

EP    2298179 A2    3/2011

OTHER PUBLICATIONS

Shulock et al.; U.S. Appl. No. 17/127,598 entitled "Patella tendon realignment implant with fixation," filed Dec. 18, 2020.

(Continued)

*Primary Examiner* — Keri J Nelson
*Assistant Examiner* — Cassidy N Stuhlsatz
(74) *Attorney, Agent, or Firm* — Fredrikson & Byron, P.A.

(57) ABSTRACT

An orthopedic implant with an inferior portion having a tibia contact surface configured to extend over a tibia; a superior portion opposite to the inferior portion having a tendon contact surface configured to change a position of a patellar tendon by lifting or tilting the patellar tendon when the curved surface of the first portion is engaged with the tibia; and a fixation mechanism adapted to attach the orthopedic implant to the tibia, the orthopedic implant being further configured to change shape from a first configuration to a second configuration in response to a load applied between the tendon contact surface and the tibia contact surface. The invention also addresses corresponding methods.

14 Claims, 3 Drawing Sheets

(56) References Cited

U.S. PATENT DOCUMENTS

| | | |
|---|---|---|
| 4,007,495 A | 2/1977 | Frazier |
| 4,041,550 A | 8/1977 | Frazier |
| 4,052,753 A | 10/1977 | Dedo |
| 4,069,518 A | 1/1978 | Groth et al. |
| 4,156,944 A | 6/1979 | Schreiber et al. |
| 4,158,894 A | 6/1979 | Worrell |
| 4,164,793 A | 8/1979 | Swanson |
| 4,285,070 A | 8/1981 | Averill |
| 4,470,158 A | 9/1984 | Pappas et al. |
| 4,642,122 A | 2/1987 | Steffee |
| 4,650,490 A | 3/1987 | Figgie |
| 4,759,766 A | 7/1988 | Janz et al. |
| 4,904,261 A | 2/1990 | Dove et al. |
| 4,955,915 A | 9/1990 | Swanson |
| 5,019,104 A | 5/1991 | Whiteside et al. |
| 5,035,700 A | 7/1991 | Kenna |
| 5,152,790 A | 10/1992 | Rosenberg et al. |
| 5,197,986 A | 3/1993 | Mikhail |
| 5,231,977 A | 8/1993 | Graston |
| 5,258,032 A | 11/1993 | Bertin |
| 5,314,481 A | 5/1994 | Bianco |
| 5,326,364 A | 7/1994 | Clift et al. |
| 5,383,937 A | 1/1995 | Mikhail |
| 5,425,775 A | 6/1995 | Kovacevic et al. |
| 5,480,443 A | 1/1996 | Elias |
| 5,544,993 A | 8/1996 | Harle |
| 5,545,229 A | 8/1996 | Parsons et al. |
| 5,571,139 A | 11/1996 | Jenkins |
| 5,571,198 A | 11/1996 | Drucker et al. |
| 5,580,353 A | 12/1996 | Mendes et al. |
| 5,643,272 A | 7/1997 | Haines et al. |
| 5,676,667 A | 10/1997 | Hausman |
| 5,702,460 A | 12/1997 | Carls et al. |
| 5,702,465 A | 12/1997 | Burkinshaw |
| 5,702,467 A | 12/1997 | Gabriel et al. |
| 5,733,287 A | 3/1998 | Tepic et al. |
| 5,824,106 A | 10/1998 | Fournol |
| 5,879,386 A | 3/1999 | Jore |
| 5,888,203 A | 3/1999 | Goldberg |
| 6,132,468 A | 10/2000 | Mansmann |
| 6,143,032 A | 11/2000 | Schafer et al. |
| 6,146,423 A | 11/2000 | Cohen et al. |
| 6,200,347 B1 | 3/2001 | Anderson et al. |
| 6,245,110 B1 | 6/2001 | Grundei et al. |
| 6,280,474 B1 | 8/2001 | Cassidy et al. |
| 6,302,915 B1 | 10/2001 | Cooney et al. |
| 6,315,798 B1 | 11/2001 | Ashby et al. |
| 6,368,326 B1 | 4/2002 | Dakin et al. |
| 6,371,985 B1 | 4/2002 | Goldberg |
| 6,409,767 B1 | 6/2002 | Pericéet al. |
| 6,468,314 B2 | 10/2002 | Schwartz et al. |
| 6,520,964 B2 | 2/2003 | Tallarida et al. |
| 6,527,794 B1 | 3/2003 | McDevitt et al. |
| 6,579,318 B2 | 6/2003 | Varga et al. |
| 6,589,248 B1 | 7/2003 | Hughes |
| 6,592,622 B1 | 7/2003 | Ferguson |
| 6,599,321 B2 | 7/2003 | Hyde |
| 6,616,696 B1 | 9/2003 | Merchant |
| 6,626,945 B2 | 9/2003 | Simon et al. |
| 6,632,247 B2 | 10/2003 | Boyer et al. |
| 6,679,914 B1 | 1/2004 | Gabbay |
| 6,702,821 B2 | 3/2004 | Bonutti |
| 6,709,460 B2 | 3/2004 | Merchant |
| 6,712,856 B1 | 3/2004 | Carignan et al. |
| 6,719,794 B2 | 4/2004 | Gerber et al. |
| 6,800,094 B2 | 10/2004 | Burkinshaw |
| 6,814,757 B2 | 11/2004 | Kopylov et al. |
| 6,824,567 B2 | 11/2004 | Tornier et al. |
| 6,852,330 B2 | 2/2005 | Bowman et al. |
| 6,854,330 B2 | 2/2005 | Potter |
| 6,855,150 B1 | 2/2005 | Linehan |
| 6,866,684 B2 | 3/2005 | Fell et al. |
| 6,890,358 B2 | 5/2005 | Ball et al. |
| 6,893,463 B2 | 5/2005 | Fell et al. |
| 6,896,702 B2 | 5/2005 | Collazo |
| 6,905,513 B1 | 6/2005 | Metzger |
| 6,911,044 B2 | 6/2005 | Fell et al. |
| 6,916,341 B2 | 7/2005 | Rolston |
| 6,926,739 B1 | 8/2005 | O'Connor et al. |
| 6,966,928 B2 | 11/2005 | Fell et al. |
| 6,974,480 B2 | 12/2005 | Messerli et al. |
| 6,994,730 B2 | 2/2006 | Posner |
| 7,004,971 B2 | 2/2006 | Serhan et al. |
| 7,008,452 B2 | 3/2006 | Hawkins |
| 7,011,687 B2 | 3/2006 | Deffenbaugh et al. |
| 7,025,790 B2 | 4/2006 | Parks et al. |
| 7,060,073 B2 | 6/2006 | Frey et al. |
| 7,105,025 B2 | 9/2006 | Castro et al. |
| 7,105,027 B2 | 9/2006 | Lipman et al. |
| 7,124,762 B2 | 10/2006 | Carter et al. |
| 7,160,333 B2 | 1/2007 | Plouhar et al. |
| 7,163,563 B2 | 1/2007 | Schwartz et al. |
| 7,182,787 B2 | 2/2007 | Hassler et al. |
| 7,226,482 B2 | 6/2007 | Messerli et al. |
| 7,291,169 B2 | 11/2007 | Hodorek |
| 7,297,161 B2 | 11/2007 | Fell |
| 7,323,012 B1 | 1/2008 | Stone et al. |
| 7,341,602 B2 | 3/2008 | Fell et al. |
| 7,476,225 B2 | 1/2009 | Cole |
| 7,479,160 B2 | 1/2009 | Branch et al. |
| 7,485,147 B2 | 2/2009 | Pappas et al. |
| 7,500,991 B2 | 3/2009 | Bartish et al. |
| 7,534,270 B2 | 5/2009 | Ball |
| 7,544,210 B2 | 6/2009 | Schaefer et al. |
| 7,572,291 B2 | 8/2009 | Gil et al. |
| 7,618,454 B2 | 11/2009 | Bentley et al. |
| 7,632,311 B2 | 12/2009 | Seedhom et al. |
| 7,637,953 B2 | 12/2009 | Branch et al. |
| 7,641,689 B2 | 1/2010 | Fell et al. |
| 7,722,676 B2 | 5/2010 | Hanson et al. |
| 7,723,395 B2 | 5/2010 | Ringeisen et al. |
| 7,726,319 B1 | 6/2010 | Boyce |
| 7,749,276 B2 | 7/2010 | Fitz |
| 7,758,651 B2 | 7/2010 | Chauhan et al. |
| 7,780,670 B2 | 8/2010 | Bonutti |
| 7,806,898 B2 | 10/2010 | Justin et al. |
| 7,815,645 B2 | 10/2010 | Haines |
| 7,819,918 B2 | 10/2010 | Malaviya et al. |
| 7,875,082 B2 | 1/2011 | Naidu |
| 7,879,105 B2 | 2/2011 | Schmieding et al. |
| 7,896,921 B2 | 3/2011 | Smith et al. |
| 7,896,923 B2 | 3/2011 | Blackwell et al. |
| 7,959,675 B2 | 6/2011 | Gately |
| 7,967,863 B2 | 6/2011 | Frey et al. |
| 7,972,383 B2 | 7/2011 | Goldstein et al. |
| 7,993,402 B2 | 8/2011 | Sidler |
| 8,002,833 B2 | 8/2011 | Fabris Monterumici et al. |
| 8,002,837 B2 | 8/2011 | Stream et al. |
| 8,002,841 B2 | 8/2011 | Hasselman |
| 8,034,117 B2 | 10/2011 | Matsuzaki et al. |
| 8,043,375 B2 | 10/2011 | Strzepa et al. |
| 8,043,380 B1 | 10/2011 | Park et al. |
| 8,052,753 B2 | 11/2011 | Melvin |
| 8,052,755 B2 | 11/2011 | Naidu |
| 8,083,746 B2 | 12/2011 | Novak |
| 8,088,168 B2 | 1/2012 | Hassler et al. |
| 8,092,544 B2 | 1/2012 | Wright et al. |
| 8,114,156 B2 | 2/2012 | Hatch |
| 8,128,704 B2 | 3/2012 | Brown et al. |
| 8,142,503 B2 | 3/2012 | Malone |
| 8,257,444 B2 | 9/2012 | Linares |
| 8,372,078 B2 | 2/2013 | Collazo |
| 8,597,362 B2 | 12/2013 | Shenoy et al. |
| 9,278,004 B2 | 3/2016 | Shenoy et al. |
| 9,808,287 B2 | 11/2017 | Halbrecht |
| 9,808,289 B2 | 11/2017 | Ross et al. |
| 10,034,679 B1 | 7/2018 | Boyer et al. |
| 10,918,415 B2 | 2/2021 | Halbrecht |
| 10,918,416 B2 | 2/2021 | Halbrecht |
| 2001/0023371 A1 | 9/2001 | Bonutti |
| 2002/0029084 A1 | 3/2002 | Paul et al. |
| 2002/0091447 A1 | 7/2002 | Shimp et al. |
| 2002/0107574 A1 | 8/2002 | Boehm et al. |
| 2002/0133230 A1 | 9/2002 | Repicci |

(56) References Cited

U.S. PATENT DOCUMENTS

| | | |
|---|---|---|
| 2003/0083751 A1 | 5/2003 | Tornier |
| 2003/0088315 A1 | 5/2003 | Supinski |
| 2003/0100950 A1 | 5/2003 | Moret |
| 2003/0109928 A1 | 6/2003 | Pasquet et al. |
| 2003/0120344 A1 | 6/2003 | Michelson |
| 2003/0120346 A1 | 6/2003 | Mercinek et al. |
| 2003/0125807 A1 | 7/2003 | Lambrecht et al. |
| 2003/0138329 A1 | 7/2003 | Koyano et al. |
| 2003/0171757 A1 | 9/2003 | Coon et al. |
| 2003/0204265 A1 | 10/2003 | Short et al. |
| 2004/0039395 A1 | 2/2004 | Coon et al. |
| 2004/0117020 A1 | 6/2004 | Frey et al. |
| 2004/0133278 A1 | 7/2004 | Marino et al. |
| 2004/0143336 A1 | 7/2004 | Burkinshaw |
| 2004/0143338 A1 | 7/2004 | Burkinshaw et al. |
| 2004/0186585 A1 | 9/2004 | Feiwell |
| 2004/0215195 A1 | 10/2004 | Shipp et al. |
| 2004/0230303 A1 | 11/2004 | Gomes et al. |
| 2004/0230315 A1 | 11/2004 | Ek |
| 2004/0236428 A1 | 11/2004 | Burkinshaw et al. |
| 2004/0243240 A1 | 12/2004 | Beaurain et al. |
| 2005/0004671 A1 | 1/2005 | Ross et al. |
| 2005/0027360 A1 | 2/2005 | Webb et al. |
| 2005/0033424 A1 | 2/2005 | Fell |
| 2005/0033426 A1 | 2/2005 | Ogilvie et al. |
| 2005/0137708 A1 | 6/2005 | Clark |
| 2005/0143822 A1 | 6/2005 | Paul |
| 2005/0222685 A1 | 10/2005 | Hayden et al. |
| 2005/0267584 A1 | 12/2005 | Burdulis et al. |
| 2005/0288788 A1 | 12/2005 | Dougherty Shah |
| 2006/0036321 A1 | 2/2006 | Henninger et al. |
| 2006/0074423 A1 | 4/2006 | Alleyne et al. |
| 2006/0074492 A1 | 4/2006 | Frey |
| 2006/0100715 A1 | 5/2006 | De Villiers |
| 2006/0129243 A1 | 6/2006 | Wong et al. |
| 2006/0142858 A1 | 6/2006 | Colleran et al. |
| 2006/0161260 A1 | 7/2006 | Thomas et al. |
| 2006/0276907 A1 | 12/2006 | Boyer et al. |
| 2007/0027547 A1 | 2/2007 | Rydell et al. |
| 2007/0129809 A1 | 6/2007 | Meridew et al. |
| 2007/0173946 A1 | 7/2007 | Bonutti |
| 2007/0203581 A1 | 8/2007 | Vanaclocha |
| 2007/0208343 A1 | 9/2007 | Magerl et al. |
| 2007/0233141 A1 | 10/2007 | Park et al. |
| 2007/0265708 A1 | 11/2007 | Brown et al. |
| 2007/0293947 A1 | 12/2007 | Mansmann |
| 2007/0299528 A9 | 12/2007 | Lotke |
| 2008/0021566 A1 | 1/2008 | Peters et al. |
| 2008/0091270 A1 | 4/2008 | Miller et al. |
| 2008/0097617 A1 | 4/2008 | Fellinger et al. |
| 2008/0140094 A1 | 6/2008 | Schwartz et al. |
| 2008/0154267 A1 | 6/2008 | Merchant et al. |
| 2008/0154311 A1 | 6/2008 | Staeubli |
| 2008/0154371 A1 | 6/2008 | Fell et al. |
| 2008/0161815 A1 | 7/2008 | Schoenefeld et al. |
| 2008/0161933 A1 | 7/2008 | Grotz et al. |
| 2008/0172054 A1 | 7/2008 | Claypool et al. |
| 2008/0195099 A1 | 8/2008 | Minas |
| 2008/0234762 A1 | 9/2008 | Forstein et al. |
| 2008/0262618 A1 | 10/2008 | Hermsen et al. |
| 2008/0281422 A1 | 11/2008 | Schmieding |
| 2008/0281425 A1 | 11/2008 | Thalgott et al. |
| 2009/0012615 A1 | 1/2009 | Fell |
| 2009/0088763 A1 | 4/2009 | Aram et al. |
| 2009/0088846 A1 | 4/2009 | Myung et al. |
| 2009/0118830 A1 | 5/2009 | Fell |
| 2009/0130167 A1 | 5/2009 | Shelton et al. |
| 2009/0164014 A1 | 6/2009 | Liljensten et al. |
| 2009/0182433 A1 | 7/2009 | Reiley et al. |
| 2009/0198341 A1 | 8/2009 | Choi et al. |
| 2009/0210063 A1 | 8/2009 | Barrett |
| 2009/0226068 A1 | 9/2009 | Fitz et al. |
| 2009/0259311 A1 | 10/2009 | Shterling et al. |
| 2009/0259312 A1 | 10/2009 | Shterling et al. |
| 2009/0306783 A1 | 12/2009 | Blum |
| 2009/0312807 A1 | 12/2009 | Boudreault et al. |
| 2010/0023126 A1 | 1/2010 | Grotz |
| 2010/0049322 A1 | 2/2010 | Mckay |
| 2010/0049325 A1 | 2/2010 | Biedermann et al. |
| 2010/0057216 A1 | 3/2010 | Gannoe et al. |
| 2010/0121355 A1 | 5/2010 | Gittings et al. |
| 2010/0125266 A1 | 5/2010 | Deem et al. |
| 2010/0131069 A1 | 5/2010 | Halbrecht |
| 2010/0161057 A1 | 6/2010 | Berry et al. |
| 2010/0198354 A1 | 8/2010 | Halbrecht |
| 2010/0204798 A1 | 8/2010 | Gerbec et al. |
| 2010/0262246 A1 | 10/2010 | Attia |
| 2010/0292731 A1 | 11/2010 | Gittings et al. |
| 2010/0292733 A1 | 11/2010 | Hendricksen et al. |
| 2010/0305698 A1 | 12/2010 | Metzger et al. |
| 2011/0004305 A1 | 1/2011 | Jansson et al. |
| 2011/0054627 A1 | 3/2011 | Bear |
| 2011/0093073 A1 | 4/2011 | Gatt et al. |
| 2011/0172768 A1 | 7/2011 | Cragg et al. |
| 2011/0202138 A1 | 8/2011 | Shenoy et al. |
| 2011/0213466 A1 | 9/2011 | Shenoy et al. |
| 2011/0238180 A1 | 9/2011 | Fritz et al. |
| 2011/0264216 A1 | 10/2011 | Makower et al. |
| 2011/0270393 A1 | 11/2011 | Marvel |
| 2011/0288643 A1 | 11/2011 | Linder-Ganz et al. |
| 2012/0022649 A1 | 1/2012 | Robinson et al. |
| 2012/0065640 A1 | 3/2012 | Metzger et al. |
| 2012/0191204 A1 | 7/2012 | Bae et al. |
| 2013/0060343 A1 | 3/2013 | Halbrecht |
| 2013/0131802 A1 | 5/2013 | Halbrecht |
| 2013/0150977 A1* | 6/2013 | Gabriel ............... A61F 2/28 623/20.32 |
| 2013/0190886 A1 | 7/2013 | Tepic et al. |
| 2013/0304208 A1 | 11/2013 | Clifford et al. |
| 2014/0156005 A1* | 6/2014 | Shenoy ............. A61F 2/3886 623/13.12 |
| 2014/0277444 A1 | 9/2014 | Clifford et al. |
| 2015/0196325 A1* | 7/2015 | Shenoy ............. A61B 17/8061 623/13.12 |
| 2018/0028229 A1 | 2/2018 | Halbrecht |
| 2018/0214261 A1 | 8/2018 | Treacy et al. |
| 2019/0099273 A1* | 4/2019 | Servidio ............. A61F 2/30749 |
| 2021/0346165 A1 | 11/2021 | Shulock et al. |

OTHER PUBLICATIONS

Chow et al.; Fracture of the tibial tubercle in the adolescent; The Journal of Bone and Joint Surgery; 72(2); pp. 231-234; Mar. 1, 1990.

Gaasbeek et al.; The influence of open and closed high tibial osteotomy on dynamic patellar tracking: a biomechanical study; Knee surg. Sports Traumatol. Arthrosc.; 15(8); pp. 978-984; Aug. 1, 2007.

Maquet; Biomechanical treatment of patellofemoral osteoarthritis. Advancement of the patellar tendon: review of rheumatism and osteoarticular diseases, National Library of Medicine; vol. 30; issue 12; pp. 780-785; (year of pub. sufficiently earlier than effective US filing date and any foreign priority date) 1963.

Zimmer; Nex Gen trabecular metal augmentation patella, Surgical technique; 4 pages; retrieved from the internet (http://www.zimmer.com/content/dam/zimmer-web/documents/en-US/pdf/surgical-techniques/knee/NexGen-Trabecular-Metal-Augmentation-Patella-Surgical-Technique-97-7255-004-00-Rev-24-2008.pdf) on Dec. 29, 2017.

* cited by examiner

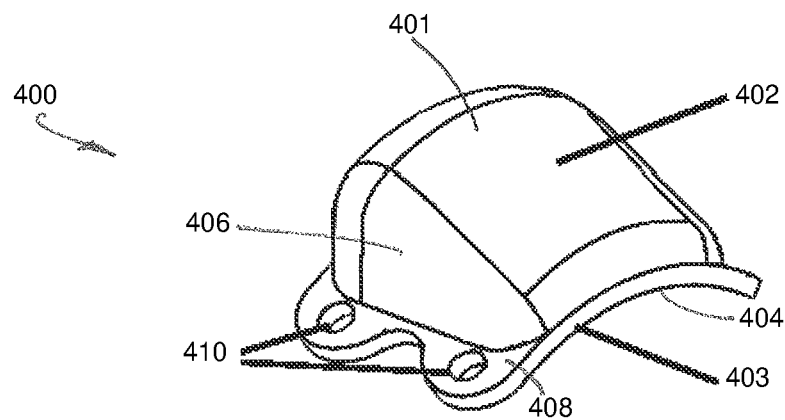
FIG. 4
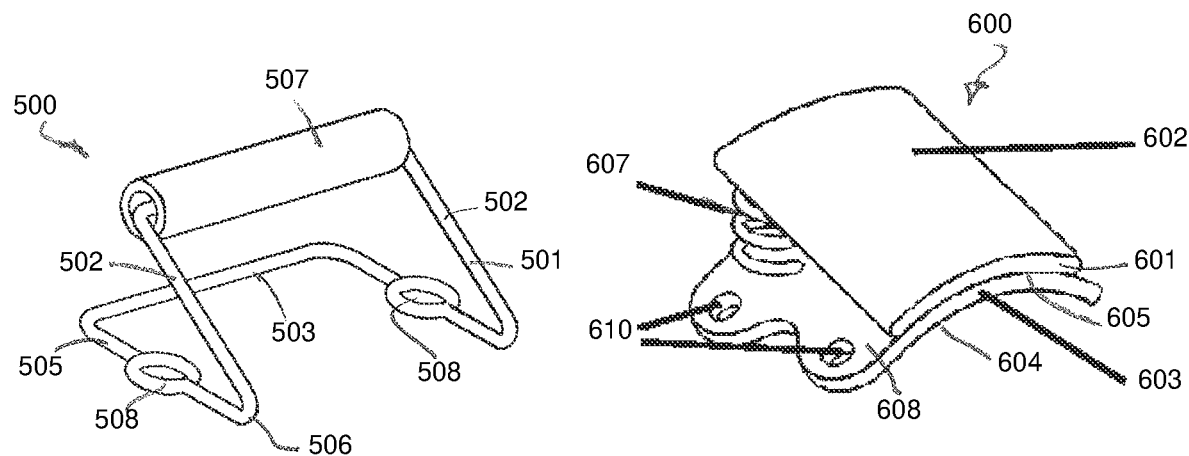
FIG. 5
FIG. 6

PATELLA TENDON REALIGNMENT IMPLANT WITH CHANGEABLE SHAPE

CROSS-REFERENCE TO RELATED APPLICATIONS

This application claims the benefit of priority of U.S. Provisional Application No. 62/956,562, filed Jan. 2, 2020, herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Problems of the patella-femoral joint are a common cause of knee pain. The pain may arise from issues such as poor alignment of the patella or from cartilage breakdown (chondromalacia or arthritis) behind the patella or on the opposing articular surface of the femoral groove (trochlea). Conventional surgical options for treating patella-femoral pain caused by malalignment, chondromalacia or arthritis may include realignment of the patella. For example tracking of the patella may be changed by tilting the patella or by moving the patella to one side or the other. Moving the patella forward (i.e., anteriorly) through a surgical procedure provides another conventional option for treating these conditions. This conventional technique is thought to decrease force across the patella-femoral joint and thus diminish the pain arising from excess force against a worn-out patellar or trochlear cartilage.

Although available, surgical options to realign the patella may be very invasive. For example, surgeries may involve cutting and fixating the bony attachment of the patellar tendon. In particular, conventional techniques may include detaching the patellar tendon from the tibia, then reattaching the patellar tendon at a new location to obtain the desired alignment of the patella. Such invasive surgical techniques may also result in prolonged recovery times. Consequently, an improved mechanism for treating patella-femoral joint problems such as patella-femoral pain, chondromalacia, and/or arthritis is desired.

U.S. Pat. No. 9,808,289 discloses embodiments of a patellar tendon realignment implant configured to be placed between the patellar tendon and the tibia in proximity to the patella to elevate and/or tilt the patellar tendon. Each of the implants described in the '289 patent maintains its shape despite changes to the load applied to it by the patellar tendon.

SUMMARY OF THE DISCLOSURE

Some activities result in higher tension or compression of the patellar tendon. For example, stair climbing and jumping increase the tension on the patellar tendon, and kneeling or sudden impacts to the knee increase patellar tendon compression. It may be desirable to temporarily change the shape of a patellar tendon realignment implant during application of a tension load on the patellar tendon (e.g., during stair climbing, jumping, etc.) or application of a compression load on the patellar tendon (e.g., during kneeling, a sudden impact to the knee, etc.).

One aspect of the invention provides an orthopedic implant having an inferior portion having a tibia contact surface configured to extend over a tibia; a superior portion opposite to the inferior portion having a tendon contact surface configured to change a position of a patellar tendon by lifting or tilting the patellar tendon when the curved surface of the first portion is engaged with the tibia; and a fixation mechanism adapted to attach the orthopedic implant to the tibia, the orthopedic implant being further configured to change shape from a first configuration to a second configuration in response to a load applied between the tendon contact surface and the tibia contact surface.

In some embodiments, the distance between the tendon contact surface and the tibia contact surface is less in the second configuration than in the first configuration. For example, the distance between the tendon contact surface and the tibia contact surface may be up to 75% less, or ⅔ less, or 50% less in the second configuration than in the first configuration.

In some or all of these embodiments, the first configuration is an unloaded configuration. Alternatively, in some or all of these embodiments, the first configuration may be a partially loaded configuration.

In some or all of these embodiments, the superior portion may include a flexible material. In some such embodiments, the orthopedic implant may also have a first lateral side disposed between the inferior portion and the superior portion; and a second lateral side disposed between the inferior portion and the superior portion opposite to the first lateral side, wherein at least one of the first lateral side and the second lateral side comprises flexible material. In some other embodiments in which the orthopedic implant has a first lateral side disposed between the inferior portion and the superior portion; a second lateral side disposed between the inferior portion and the superior portion opposite to the first lateral side, the orthopedic implant may also have a central chamber defined by the superior portion, the inferior portion, the first lateral side and the second lateral side. In such embodiments, the central chamber comprises a gas or an elastic material.

In some embodiments, the orthopedic implant also has a cantilever connection between the superior portion and the inferior portion at an anterior side of the orthopedic implant, the superior portion being movable at the cantilever connection with respect to the inferior portion. In some such embodiments, the orthopedic implant has a posterior side opposite to the anterior side, the posterior side comprising an opening between the superior portion and the inferior portion, the opening having a height that changes as the superior portion moves at the cantilever connection with respect to the inferior portion. In other embodiments in which the orthopedic implant has a first lateral side and a second lateral side opposite to the first lateral side, the first lateral side and the second lateral side each have an opening between the superior portion and the inferior portion.

In some embodiments, the orthopedic implant includes deformable material. In some such embodiments, the superior portion has deformable material, and the inferior portion may also have a rigid material. In such embodiments, the fixation mechanism may include screw holes in the inferior portion. In some embodiments, the orthopedic implant also has a first lateral side disposed between the inferior portion and the superior portion and a second lateral side disposed between the inferior portion and the superior portion opposite to the first lateral side, and at least one of the first lateral portion and the second lateral portion has deformable material.

In some embodiments, the orthopedic implant has a spring operatively disposed between the superior portion and the inferior portion to permit the superior portion to move with respect to the inferior portion in response to a load applied between the tendon contact surface and the tibia contact surface. In some such embodiments, the spring is a cantilever spring connecting the superior portion to the inferior portion. For example, in some embodiments the inferior portion and the superior portion together comprise a wire spring form. In some such embodiments, the superior portion may have a roller. In other embodiments, the orthopedic implant may have a hinge connecting the superior portion to the inferior portion, and the spring may optionally be disposed between the superior portion and the inferior portion.

Yet another aspect of the invention provides a method for repositioning a patellar tendon. In some embodiments, the method includes the steps of: inserting an orthopedic implant in a first configuration between the patellar tendon and a tibia; engaging a tibia engagement surface of an inferior portion of the orthopedic implant with the tibia; engaging a patellar tendon surface of a superior portion of the orthopedic implant with the patellar tendon; changing a position of the patellar tendon; affixing the orthopedic implant to the tibia; and, in response to a load applied to the orthopedic implant by the patellar tendon, changing a shape of the orthopedic implant from the first configuration to a second configuration In some embodiments, the method includes the step of changing the shape of the orthopedic implant from the second configuration to the first configuration after removal of the load. In some or all of these embodiments, the step of changing a shape includes the step of reducing a distance between the tendon contact surface and the tibia contact surface. For example, the distance between the tendon contact surface and the tibia contact surface is up to 75% less in the second configuration than in the first configuration, or up to ⅔ less in the second configuration than in the first configuration, or up to 50% less in the second configuration than in the first configuration.

In some or all of these embodiments, the first configuration may be an unloaded configuration or a partially loaded configuration.

In some or all of these embodiments, the step of changing a shape may include the step of deforming at least a portion of the orthopedic implant. In some such embodiments, the step of deforming at least a portion of the orthopedic implant may include the step of deforming the superior portion. In some such embodiments in which the implant comprises a first lateral side disposed between the inferior portion and the superior portion and a second lateral side disposed between the inferior portion and the superior portion opposite to the first lateral side, the step of deforming at least a portion of the orthopedic implant may include the step of deforming at least one of the first lateral side and the second lateral side.

In some or all of these embodiments, the step of changing a shape may include the step of moving the patellar tendon surface and the tibia contact surface with respect to each other against a cantilever connection of the orthopedic implant.

In some or all of these embodiments, the step of changing a shape may include the step of moving the patellar tendon surface and the tibia contact surface with respect to each other against a spring of the orthopedic implant.

In some or all of these embodiments, the step of changing a shape may include the step of moving the patellar tendon surface and the tibia contact surface with respect to each other about a hinge of the orthopedic implant.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4 is a perspective view of yet another embodiment of a patellar implant.

FIG. 5 is a perspective view of still another embodiment of a patellar implant.

FIG. 6 is a perspective view of another embodiment of a patellar implant.

DETAILED DESCRIPTION

Figure 1A:
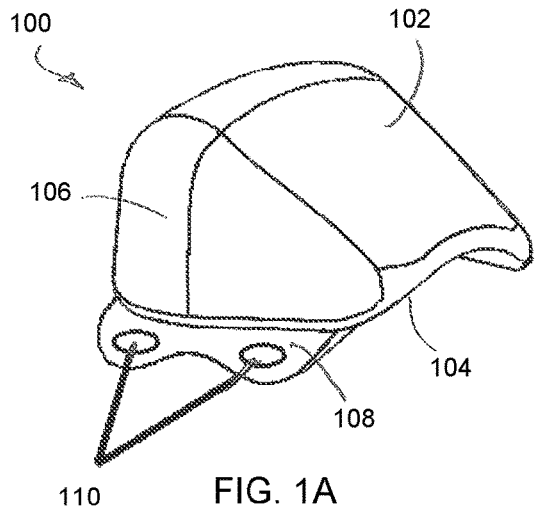
FIG. 1A is a perspective view of an embodiment of a patellar implant.
Figure 1B:
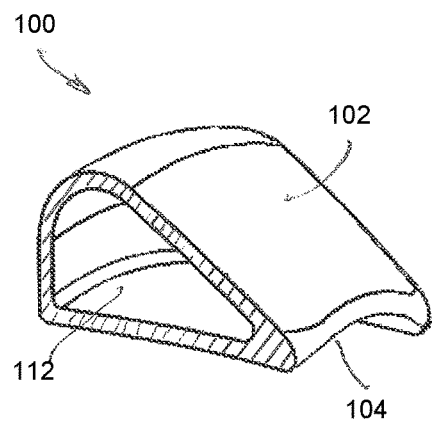
FIG. 1B is a cross-sectional view of the patellar implant of FIG. 1A.

Implant 100 in FIGS. 1A and 1B has a superior portion with a tendon contact surface 102, an inferior portion with a tibia contact surface 104, a first lateral side 106 extending from the superior portion to the inferior portion, and a second lateral side (not shown) opposite to the first lateral side. A fixation tab 108 extends from the inferior portion on the first lateral side. Holes 110 in the fixation tab accommodate fixation screws or spikes (not shown). A similar fixation tab with holes extends from the inferior portion on the second lateral side as well.

Implant 100 may be implanted between a patient's patellar tendon and tibia to change the position of the patellar tendon by elevating it or lifting away from the tibia. When in place, the tibia contact surface 104 of the inferior portion is against, or in proximity to, the tibia. Tibia contact surface 104 may be curved to match the shape of the tibia. Alternatively, the tibia contact surface may be flat, and the tibia may be cut or shaved to accommodate the flat surface of the implant. When tibia contact surface 104 is in place on the tibia, tendon contact surface 102 will engage the patellar tendon to lift and/or tilt the tendon, thereby changing its position. Screws and/or spikes may be inserted through holes 110 into the tibia to hold the implant in place.

Implant 100 has a first configuration when it is placed on the tibia. The implant's shape and dimensions in this first configuration may be the same as its shape and dimensions prior to implant. Alternatively, the implant may be slightly compressed or deformed when first placed between the tibia and the patellar tendon.

After implantation, when the patient jumps or climbs stairs, tension on the patellar tendon will increase, thereby placing an increased load on implant 100. A different kind of load may be placed on implant 100 when the patient compresses the patellar tendon, such as by kneeling or encountering a sudden knee impact. Implant 100 responds to these loads by temporarily deforming to a second configuration. After the load is removed, implant 100 returns to the first configuration. This feature is provided by forming superior portion 102 and/or the lateral sides 106 of flexible material, such as rubber or plastic. In addition, a center chamber 112 surrounded in part by the superior portion 102, inferior portion 104, and the lateral sides 106 is filled with an inert gas to provide the ability to compress the implant to the second configuration and to return it to its first configuration. The flexible material's durometer and thickness, and the pressure of the inert gas inside of chamber 112, provide the necessary support for patellar tendon lift and/or tilt and as well as the ability for the implant to deform under a compressive force down to ⅓ of the implant's height in the first configuration and to return to the first configuration after removal of the compressive force. In other words, a distance between the tendon contact surface and the tibia contact surface in the second configuration is up to ⅔ less than in the first configuration.

Figure 2A:
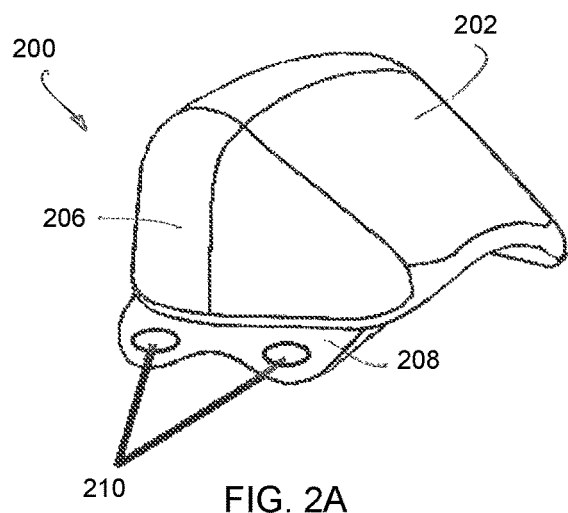
FIG. 2A is a perspective view of another embodiment of a patellar implant.
Figure 2B:
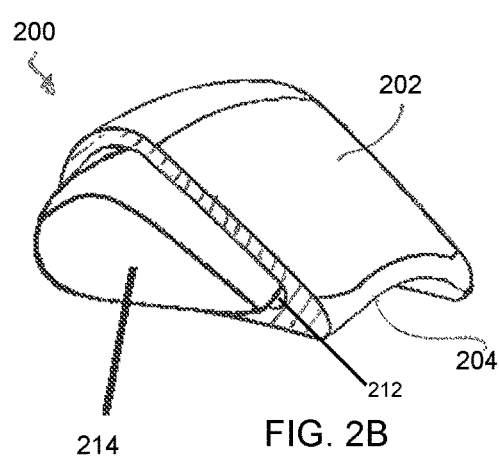
FIG. 2B is a cross-sectional view of the patellar implant of FIG. 2A.

The embodiment of FIGS. 2A and 2B is similar to that of FIGS. 1A and 1B. Implant 200 may be implanted between a patient's patellar tendon and tibia to change the position of the patellar tendon by elevating it or lifting away from the tibia. When in place, tibia contact surface 204 of the inferior portion is against, or in proximity to, the tibia. Tibia contact surface 204 may be curved to match the shape of the tibia. Alternatively, the tibia contact surface may be flat, and the tibia may be cut or shaved to accommodate the flat surface of the implant. When tibia contact surface 204 is in place on the tibia, tendon contact surface 202 will engage the patellar tendon to lift and/or tilt the tendon, thereby changing its position. Screws and/or spikes may be inserted through holes 210 of fixation tab 208 into the tibia to hold the implant in place.

Implant 200 has a first configuration when it is placed on the tibia. The implant's shape and dimensions in this first configuration may be the same as its shape and dimensions prior to implant. Alternatively, the implant may be slightly compressed or deformed when first placed between the tibia and the patellar tendon.

After implantation, when the patient jumps or climbs stairs, tension on the patellar tendon will increase, thereby placing an increased load on implant 200. A different kind of load may be placed on implant 200 when the patient compresses the patellar tendon, such as by kneeling or encountering a sudden knee impact. Implant 200 responds to these loads by temporarily deforming to a second configuration. After the load is removed, implant 200 returns to the first configuration. This feature is provided by forming superior portion 202 and/or the lateral sides 206 of flexible material, such as rubber or plastic. In addition, a center chamber 212 surrounded in part by the superior portion 202, inferior portion 204, and the lateral sides 206 is filled with a core 214 formed from an elastic material to provide the ability to compress the implant to the second configuration and to return it to its first configuration. The flexible material's durometer and thickness, and the elastic properties of core 214, provide the necessary support for patellar tendon lift and/or tilt and as well as the ability for the implant to deform under a compressive force down to ⅓ of the implant's height in the first configuration and to return to the first configuration after removal of the compressive force. In other words, a distance between the tendon contact surface and the tibia contact surface in the second configuration is up to ⅔ less than in the first configuration.

Figure 3A:
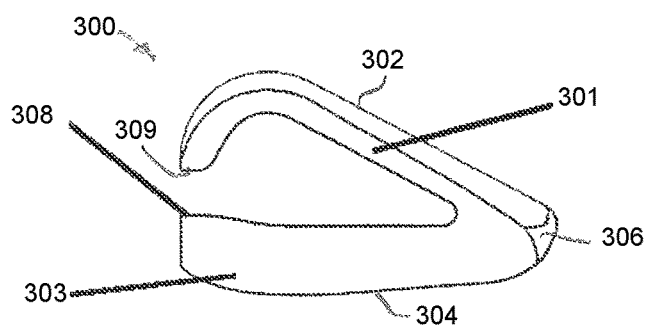
FIG. 3A is a side view of yet another embodiment of a patellar implant.
Figure 3B:
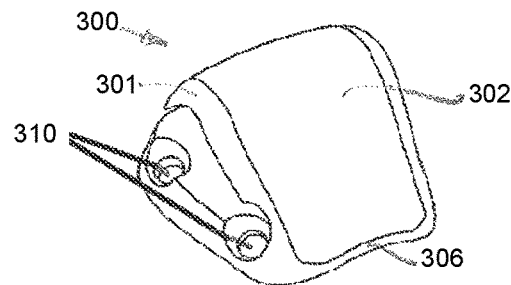
FIG. 3B is a perspective view of the implant of FIG. 3A.

FIGS. 3A and 3B show yet another embodiment of a deformable patellar implant. Implant 300 has a superior portion 301 with a tendon contact surface 302 joined at a cantilever portion 306 on the implant's anterior side to an inferior portion 303 having a tibia contact surface 304. As in the other embodiments, implant 300 may be implanted between a patient's patellar tendon and tibia to change the position of the patellar tendon by elevating it or lifting away from the tibia. When in place, tibia contact surface 304 of the inferior portion is against, or in proximity to, the tibia. Tibia contact surface 304 may be curved to match the shape of the tibia. Alternatively, the tibia contact surface may be flat, and the tibia may be cut or shaved to accommodate the flat surface of the implant. When tibia contact surface 304 is in place on the tibia, tendon contact surface 302 will engage the patellar tendon to lift and/or tilt the tendon, thereby changing its position. Screws and/or spikes may be inserted through holes 310 into the tibia to hold the implant in place.

Implant 300 has a first configuration when it is placed on the tibia. The implant's shape and dimensions in this first configuration may be the same as its shape and dimensions prior to implant. Alternatively, the implant may be slightly compressed or deformed when first placed between the tibia and the patellar tendon.

After implantation, when the patient jumps or climbs stairs, tension on the patellar tendon will increase, thereby placing an increased load on implant 300. A different kind of load may be placed on implant 300 when the patient compresses the patellar tendon, such as by kneeling or encountering a sudden knee impact. Implant 300 responds to these loads by temporarily deforming to a second configuration by flexing superior portion 301 with respect to inferior portion 303 about the cantilever portion 306. As it deforms, a gap 308 on the posterior side of implant 300 gets smaller and possibly closes altogether as surface 309 meets the top of inferior portion 303. After the load is removed, implant 300 returns to the first configuration. Implant 300 may be made of metal, plastic or a combination thereof so that it can sustain multiple flexing cycles without fatigue and breakage. The flexible material's elastic modulus and geometry are calibrated to provide the necessary support required for tendon lift and/or redirection and the necessary deformation under compressive forces.

FIG. 4 shows another embodiment of a deformable patellar implant according to the invention. Implant 400 has an inferior portion 403 with a tibia contact surface 404, a superior portion 401 with a tendon contact surface 402, a first lateral side 406 extending from the superior portion to the inferior portion, and a second lateral side (not shown) opposite to the first lateral side. A fixation tab 408 extends from the inferior portion on the first lateral side. Holes 410 in the fixation tab accommodate fixation screws or spikes (not shown). A similar fixation tab with holes extends from the inferior portion on the second lateral side as well.

Implant 400 may be implanted between a patient's patellar tendon and tibia to change the position of the patellar tendon by elevating it or lifting away from the tibia. When in place, the tibia contact surface 404 of the inferior portion is against, or in proximity to, the tibia. Tibia contact surface 404 may be curved to match the shape of the tibia. Alternatively, the tibia contact surface may be flat, and the tibia may be cut or shaved to accommodate the flat surface of the implant. When tibia contact surface 404 is in place on the tibia, tendon contact surface 402 will engage the patellar tendon to lift and/or tilt the tendon, thereby changing its position. Screws and/or spikes may be inserted through holes 410 into the tibia to hold the implant in place.

Implant 400 has a first configuration when it is placed on the tibia. The implant's shape and dimensions in this first configuration may be the same as its shape and dimensions prior to implant. Alternatively, the implant may be slightly compressed or deformed when first placed between the tibia and the patellar tendon.

After implantation, when the patient jumps or climbs stairs, tension on the patellar tendon will increase, thereby placing an increased load on implant 400. A different kind of load may be placed on implant 400 when the patient compresses the patellar tendon, such as by kneeling or encountering a sudden knee impact. Implant 400 responds to these loads by temporarily deforming to a second configuration. After the load is removed, implant 400 returns to the first configuration. This feature is provided by forming the superior portion 401 and/or the lateral sides 406 of soft and deformable material, such as silicone rubber. Inferior portion 403, on the other hand, is rigid plastic or metal. The deformable portions (superior portion 401 and/or lateral sides 406) have a durometer and geometry calibrated to provide the support needed for tendon lift and/or redirection, and under compressive forces can deform down to ½ of the implant's original height in the first configuration and to return to the first configuration after removal of the compressive force. In other words, a distance between the tendon contact surface and the tibia contact surface in the second configuration is up to 50% less than in the first configuration.

FIG. 5 shows still another embodiment of a deformable patellar implant. Implant 500 has a wire spring form 501 made of, e.g., spring-tempered stainless steel or titanium. Spring form 501 extends from an inferior posterior portion 503 and two inferior side portions 505 to cantilever sections 506. The underside of inferior posterior portion 503 and the inferior side portions 505 together form a tibia contact surface. Two superior side portions 502 extend upwards from cantilever sections 506 to a posterior roller 507, which provides a tendon contact surface. Screw mounts 508 extend from inferior side portions 505 and can accommodate fixation screws or spikes.

Implant 500 may be implanted between a patient's patellar tendon and tibia to change the position of the patellar tendon by elevating it or lifting away from the tibia. When in place, the tibia contact surface is against, or in proximity to, the tibia. When the tibia contact surface is in place on the tibia, roller 507 will engage the patellar tendon to lift and/or tilt the tendon, thereby changing its position. Screws and/or spikes may be inserted through screw mounts 508 into the tibia to hold the implant in place.

Implant 500 has a first configuration when it is placed on the tibia. The implant's shape and dimensions in this first configuration may be the same as its shape and dimensions prior to implant. Alternatively, the implant may be slightly compressed or deformed when first placed between the tibia and the patellar tendon.

After implantation, when the patient jumps or climbs stairs, tension on the patellar tendon will increase, thereby placing an increased load on implant 500. A different kind of load may be placed on implant 500 when the patient compresses the patellar tendon, such as by kneeling or encountering a sudden knee impact. Implant 500 responds to these loads by temporarily deforming to a second configuration. After the load is removed, implant 500 returns to the first configuration. The spring form material, temper condition, and geometry are calibrated together to provide the support needed to lift and/or redirect the patellar tendon. Under compressive forces, the implant 500 can deform down to ¼ of the implant's original height in the first configuration and to return to the first configuration after removal of the compressive force. In other words, a distance between the tendon contact surface and the tibia contact surface in the second configuration is up to 75% less than in the first configuration.

FIG. 6 shows an embodiment of a patellar implant in which a superior portion 601 connects to an inferior portion 603 via a hinge 605 and a spring 607. Superior portion 601 has a tendon contact surface 602, and inferior portion 603 has a tibia contact surface 604. A fixation tab 608 extends from the inferior portion on both lateral sides. Holes 610 in the fixation tab accommodate fixation screws or spikes (not shown). The superior portion 601 and inferior portion 603 may be made from rigid plastic or metal.

Implant 600 may be may be implanted between a patient's patellar tendon and tibia to change the position of the patellar tendon by elevating it or lifting away from the tibia. When in place, the tibia contact surface 604 of the inferior portion is against, or in proximity to, the tibia. Tibia contact surface 604 may be curved to match the shape of the tibia. Alternatively, the tibia contact surface may be flat, and the tibia may be cut or shaved to accommodate the flat surface of the implant. When tibia contact surface 604 is in place on the tibia, tendon contact surface 602 will engage the patellar tendon to lift and/or tilt the tendon, thereby changing its position. Screws and/or spikes may be inserted through holes 610 into the tibia to hold the implant in place.

Implant 600 has a first configuration when it is placed on the tibia. The implant's shape and dimensions in this first configuration may be the same as its shape and dimensions prior to implant. Alternatively, the implant may be slightly compressed or deformed when first placed between the tibia and the patellar tendon.

After implantation, when the patient jumps or climbs stairs, tension on the patellar tendon will increase, thereby placing an increased load on implant 600. A different kind of load may be placed on implant 600 when the patient compresses the patellar tendon, such as by kneeling or encountering a sudden knee impact. Implant 600 responds to these loads by moving superior portion 601 about hinge 605 away from inferior portion 603 and against the action of spring 607 to temporarily change the implant's shape to a second configuration. After the load is removed, spring 607 returns implant 600 to the first configuration. The spring element material, temper condition, and geometry are calibrated together to provide the necessary support for tendon lift and/or redirection as well as the ability for the implant to change shape under a compressive force down to ⅓ of the implant's height in the first configuration and to return to the first configuration after removal of the compressive force. In other words, a distance between the tendon contact surface and the tibia contact surface in the second configuration is up to ⅔ less than in the first configuration.

Figure 7A:
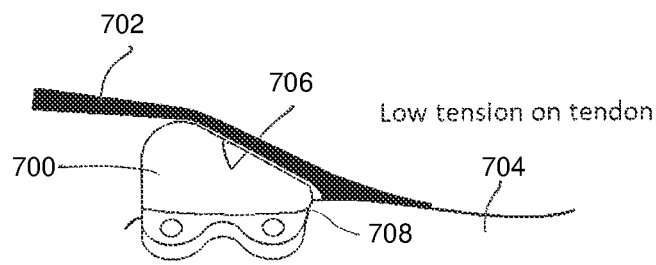
FIGS. 7A and 7B show an implant according to embodiments of this invention in use on a patient.
Figure 7B:
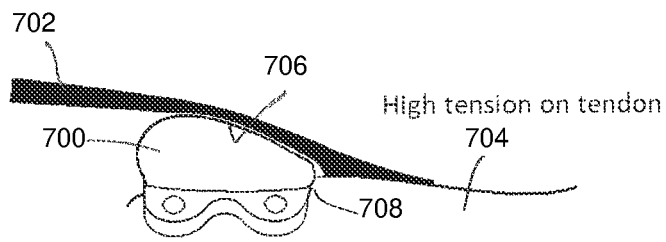

FIGS. 7A and 7B demonstrate use of an implant according to embodiments of this invention in use on a patient. Implant 700 (such as, e.g., an implant shown in FIG. 1, FIG. 2 or FIG. 4) is affixed to a tibia 704 of the patient. FIG. 7A shows the shape and configuration of the implant 700 when patellar tendon 702 is under little or no tension. FIG. 7B shows the shape and configuration of implant 700 when tendon 702 is under high tension. When under tension, tendon 702 exerts a load on implant 700 and compresses the implant to reduce the distance from the tendon contact surface 706 and the tibia contact surface 708 as shown in FIG. 7B.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for repositioning a patellar tendon, the method comprising:
   inserting an orthopedic implant in a first configuration between the patellar tendon and a tibia;
   engaging a tibia engagement surface of an inferior portion of the orthopedic implant with the tibia;
   engaging a patellar tendon contact surface of a superior portion of the orthopedic implant with the patellar tendon wherein in the first configuration a posterior side of the patellar tendon contact surface of the superior portion of the orthopedic implant is at a greater distance above the tibia engagement surface than an anterior side of the patellar tendon contact surface of the superior portion of the orthopedic implant is above the tibia engagement surface;
   changing a position of the patellar tendon;
   affixing the orthopedic implant to the tibia; and,
   in response to a load applied to the orthopedic implant by the patellar tendon, changing a shape of the orthopedic implant from the first configuration to a second configuration wherein in the second configuration the distance of the posterior side of the patellar tendon surface of the superior portion of orthopedic implant above the tibia engagement surface is reduced while still remaining at a greater distance above the tibia engagement surface than the anterior side of the patellar tendon surface of the superior surface of the orthopedic implant is above the tibia engagement surface.

2. The method of claim 1 further comprising changing the shape of the orthopedic implant from the second configuration to the first configuration after removal of the load.

3. The method of claim 1 wherein changing the shape of the orthopedic implant from the first configuration to the second configuration comprises reducing a distance between the patellar tendon contact surface of the superior portion of the orthopedic implant and the tibia engagement surface while maintaining a tilt of the patellar tendon along the orthopedic implant.

4. The method of claim 3 wherein the distance between the tendon contact surface and the tibia contact surface is up to 75% less in the second configuration than in the first configuration.

5. The method of claim 3 wherein the distance between the tendon contact surface and the tibia contact surface is up to ⅔ less in the second configuration than in the first configuration.

6. The method of claim 3 wherein the distance between the tendon contact surface and the tibia contact surface is up to 50% less in the second configuration than in the first configuration.

7. The method of claim 1 wherein the first configuration comprises an unloaded configuration.

8. The method of claim 1 wherein the first configuration comprises a partially loaded configuration.

9. The method of claim 1 wherein the step of changing the shape of the orthopedic implant comprises deforming at least a portion of the orthopedic implant.

10. The method of claim 9 wherein the step of deforming at least a portion of the orthopedic implant comprises deforming the superior portion.

11. The method of claim 9 wherein the implant comprises a first lateral side disposed between the inferior portion and the superior portion and a second lateral side disposed between the inferior portion and the superior portion opposite to the first lateral side, wherein the step of deforming at least a portion of the orthopedic implant comprises deforming at least one of the first lateral side and the second lateral side.

12. The method of claim 1 wherein the step of changing a shape comprises moving the patellar tendon surface and the tibia contact surface with respect to each other against a cantilever connection of the orthopedic implant.

13. The method of claim 1 wherein the step of changing a shape comprises moving the patellar tendon surface and the tibia contact surface with respect to each other against a spring of the orthopedic implant.

14. The method of claim 1 wherein the step of changing a shape comprises moving the patellar tendon surface and the tibia contact surface with respect to each other about a hinge of the orthopedic implant.

* * * * *